*(12)* United States Patent
Meister et al.

(10) Patent No.: US 9,776,001 B2
(45) Date of Patent: *Oct. 3, 2017

(54) INTERAURAL COHERENCE BASED COCHLEAR STIMULATION USING ADAPTED ENVELOPE PROCESSING

(71) Applicant: MED-EL Elektromedizinische Geraete GmbH, Innsbruck (AT)

(72) Inventors: Dirk Meister, Innsbruck (AT); Peter Schleich, Telfs (AT)

(73) Assignee: MED-EL Elektromedizinische Geraete GmbH, Innsbruck (AT)

( * ) Notice: Subject to any disclaimer, the term of this patent is extended or adjusted under 35 U.S.C. 154(b) by 0 days.

This patent is subject to a terminal disclaimer.

(21) Appl. No.: 15/369,081

(22) Filed: Dec. 5, 2016

(65) Prior Publication Data

US 2017/0080229 A1 Mar. 23, 2017

Related U.S. Application Data

(63) Continuation-in-part of application No. 15/178,635, filed on Jun. 10, 2016, and a continuation-in-part of application No. 15/178,768, filed on Jun. 10, 2016.

(Continued)

(51) Int. Cl.
*A61N 1/36* (2006.01)
*A61N 1/05* (2006.01)

(52) U.S. Cl.
CPC ....... *A61N 1/36032* (2013.01); *A61N 1/0541* (2013.01)

(58) Field of Classification Search
CPC ... A61N 1/36032; A61N 1/0541; H04R 25/43
See application file for complete search history.

(56) References Cited

U.S. PATENT DOCUMENTS 6,219,580 B1 4/2001 Faltys et al.
6,594,525 B1 7/2003 Zierhofer
(Continued)

FOREIGN PATENT DOCUMENTS

WO WO 2016/049403 A1 3/2016

OTHER PUBLICATIONS

Faller et al., "Source localization in complex listening situations: Selection of binaural cues based on interaural coherence," Journal of Acoustical Society of America, vol. 116, No. 5, pp. 3075-3089, Nov. 2004.

(Continued)

*Primary Examiner* — William Levicky
(74) *Attorney, Agent, or Firm* — Sunstein Kann Murphy & Timbers LLP

(57) ABSTRACT

A signal processing system is described for a bilateral hearing implant system having left side and right side hearing implants. An interaural coherence analysis module receives input signals from each hearing implant including sensing microphone signals and band pass signals, and analyzes the input signals to produce an interaural coherence signal output characterizing reverberation-related similarity of the input signals. A pulse timing and coding module for each hearing implant then processes the band pass signals to develop stimulation timing signals, wherein for one or more selected band pass signals, wherein the processing includes using an envelope gating function developed from the interaural coherence signal.

16 Claims, 14 Drawing Sheets

Related U.S. Application Data

(60) Provisional application No. 62/174,003, filed on Jun. 11, 2015, provisional application No. 62/215,187, filed on Sep. 8, 2015.

(56) References Cited

U.S. PATENT DOCUMENTS

| | | | |
|---|---|---|---|
| 7,937,155 | B1 | 5/2011 | Voelkel |
| 2008/0319509 | A1 | 12/2008 | Laback et al. |
| 2010/0198300 | A1 | 8/2010 | Smith |
| 2014/0005746 | A1 | 1/2014 | Schleich et al. |
| 2014/0074183 | A1 | 3/2014 | Kulkarni et al. |
| 2014/0200630 | A1 | 7/2014 | Mishra |
| 2014/0219486 | A1* | 8/2014 | Brown ............... H04R 25/43 381/320 |
| 2016/0015974 | A1 | 1/2016 | Milczynski |
| 2016/0106980 | A1 | 4/2016 | Sürth et al. |
| 2016/0165363 | A1 | 6/2016 | Meister et al. |
| 2016/0337779 | A1* | 11/2016 | Davidson ............ H04S 7/304 |

OTHER PUBLICATIONS

Majdak et al., "Effects of Interaural Time Differences in Fine Structure and Envelope on Lateral Discrimination in Bilateral Electrical Hearing," Acoustics Research Institute, Austrian Academy of Sciences Austria, Presented at the 28$^{th}$ Annual Midwinter Research Meeting of the Association for Research in Otolaryngology, 1 page, 2006.

Middlebrooks, "Auditory Cortex Phase Locking to Amplitude-Modulated Cochlear Implant Pulse Trains," Journal of Neurophysiol, vol. 100, pp. 76-91, Jul. 2008.

Monaghan et al., "Factors affecting the use of envelope interaural time differences in reverberation," Journal of Acoustical Society of America, vol. 133, No. 4, pp. 2288-2300, Apr. 2013.

Ruggles et al., "Why Middle-Aged Listeners Have Trouble Hearing in Everyday Settings," Current Biology, vol. 22, pp. 1417-1422, Aug. 7, 2012.

Wilson et al., "Better speech recognition with cochlear implants," Letters to Nature, vol. 352, pp. 236-238, Jul. 18, 1991.

International Searching Authority, International Search Report—International Application No. PCT/US16/36799, dated Sep. 6, 2016, together with the Written Opinion of the International Searching Authority, 20 pages.

International Searching Authority, International Search Report—International Application No. PCT/US16/36826, dated Sep. 6, 2016, together with the Written Opinion of the International Searching Authority, 18 pages.

\* cited by examiner

INTERAURAL COHERENCE BASED COCHLEAR STIMULATION USING ADAPTED ENVELOPE PROCESSING

This application is a continuation-in part of U.S. patent application Ser. No. 15/178,635, filed Jun. 10, 2016 and a continuation-in part of U.S. patent application Ser. No. 15/178,768, filed Jun. 10, 2016, both of which in turn claim priority from U.S. Provisional Patent Application 62/174,003, filed Jun. 11, 2015, and from U.S. Provisional Patent Application 62/215,187, filed Sep. 8, 2015, all of which are incorporated herein by reference in their entireties.

TECHNICAL FIELD

The present invention relates to signal processing arrangements for cochlear implants.

BACKGROUND ART

A normal human ear transmits sounds as shown in FIG. 1 through the outer ear 101 to the tympanic membrane 102 which moves the bones of the middle ear 103 that vibrate the oval window and round window openings of the cochlea 104. The cochlea 104 is a long narrow duct wound spirally about its axis for approximately two and a half turns. It includes an upper channel known as the scala vestibuli and a lower channel known as the scala tympani, which are connected by the cochlear duct. The cochlea 104 forms an upright spiraling cone with a center called the modiolar where the spiral ganglion cells of the acoustic nerve 113 reside. In response to received sounds transmitted by the middle ear 103, the fluid-filled cochlea 104 functions as a transducer to generate electric pulses which are transmitted to the cochlear nerve 113, and ultimately to the brain.

Hearing is impaired when there are problems in the ability to transduce external sounds into meaningful action potentials along the neural substrate of the cochlea 104. To improve impaired hearing, hearing prostheses have been developed. For example, when the impairment is related to operation of the middle ear 103, a conventional hearing aid may be used to provide acoustic-mechanical stimulation to the auditory system in the form of amplified sound. Or when the impairment is associated with the cochlea 104, a cochlear implant with an implanted electrode can electrically stimulate auditory nerve tissue with small currents delivered by multiple electrode contacts distributed along the electrode. Although the following discussion is specific to cochlear implants, some hearing impaired persons are better served when the stimulation electrode is implanted in other anatomical structures. Thus hearing implant systems include brainstem implants, middle brain implants, etc. each stimulating a specific auditory target in the auditory system.

FIG. 1 also shows some components of a typical cochlear implant system where an external microphone provides an audio signal input to an external implant processor 111 in which various signal processing schemes can be implemented. For example, it is well-known in the field that electrical stimulation at different locations within the cochlea 104 produce different frequency percepts. The underlying mechanism in normal acoustic hearing is referred to as the tonotopic principle. In cochlear implant users, the tonotopic organization of the cochlea has been extensively investigated; for example, see Vermeire et al., *Neural tonotopy in cochlear implants: An evaluation in unilateral cochlear implant patients with unilateral deafness and tinnitus*, Hear Res, 245(1-2), 2008 Sep. 12 p. 98-106; and Schatzer et al., *Electric-acoustic pitch comparisons in single-sided-deaf cochlear implant users: Frequency-place functions and rate pitch*, Hear Res, 309, 2014 March, p. 26-35 (both of which are incorporated herein by reference in their entireties). Examples of current signal processing approaches in the field of cochlear implants include continuous interleaved sampling (CIS) digital signal processing, channel specific sampling sequences (CSSS) digital signal processing (as described in U.S. Pat. No. 6,348,070, incorporated herein by reference), advanced combinational encoder (ACE) processing, spectral peak (SPEAK) digital signal processing, fine structure processing (FSP) and compressed analog (CA) signal processing.

Accordingly, the processed audio signal in the external implant processor 111 is converted into a digital data format for transmission by external transmitter coil 107 into an implant stimulator 108. Besides receiving the processed audio information, the implant stimulator 108 also performs additional signal processing such as error correction, pulse formation, etc., and produces stimulation signals (based on the extracted audio information) that are sent through an electrode lead 109 to an implanted electrode array 110. Typically, this electrode array 110 includes multiple electrode contacts 112 on its surface that provide selective stimulation of the cochlea 104.

In existing cochlear implant systems, the electrode contacts 112 are stimulated in a repeating time sequence of stimulation frames. If each stimulation frame uses all the electrode contacts 112, then the stimulation rate needs to be relatively low to accommodate the pulse lengths required to achieve a patient-specific sufficient loudness perception. Another drawback of stimulating all the electrode contacts 112 in a given stimulation frame is the interference between different channels due to overlapping electrical fields, residual charges at the neuron membranes, and higher order processes. There are several different approaches to reducing these negative effects which use a reduced subset of the electrode contacts 112. Channel selection then is performed frame-wise based on instantaneous signal properties such as band pass signal amplitude.

For normal hearing subjects, both the envelope and the fine time structure, are important for localization and speech understanding in noise and reverberant conditions (Zeng, Fan-Gang, et al. "Auditory perception with slowly-varying amplitude and frequency modulations." *Auditory Signal Processing*. Springer New York, 2005. 282-290; Drennan, Ward R., et al. "Effects of temporal fine structure on the lateralization of speech and on speech understanding in noise." *Journal of the Association for Research in Otolaryngology* 8.3 (2007): 373-383; and Hopkins, Kathryn, and Brian Moore. "The contribution of temporal fine structure information to the intelligibility of speech in noise." *The Journal of the Acoustical Society of America* 123.5 (2008): 3710-3710.; and all of which are hereby incorporated herein by reference in their entireties).

Older speech coding strategies mainly encode the slowly varying signal envelope information and do not transmit the fine time structure of a signal. One widespread scheme uses what is referred to as an n-of-m approach where only some number n electrode channels with the greatest amplitude are stimulated in a given stimulation frame. This approach is used, for instance, in the ACE and SPEAK strategies by Cochlear Corporation. If, for a given time frame, the amplitude of a specific electrode channel remains higher than the amplitudes of other channels, then that channel will be selected for the whole time frame. Subsequently, the number of electrode channels that are available for coding information is reduced by one, which results in a clustering of stimulation pulses.

In the CIS signal processing strategy, the signal processor only uses the band pass signal envelopes for further processing, i.e., they contain the entire stimulation information. For each electrode channel, the signal envelope is represented as a sequence of biphasic pulses at a constant repetition rate. A characteristic feature of CIS is that the stimulation rate is equal for all electrode channels and there is no relation to the center frequencies of the individual channels. It is intended that the pulse repetition rate is not a temporal cue for the patient (i.e., it should be sufficiently high so that the patient does not perceive tones with a frequency equal to the pulse repetition rate). The pulse repetition rate is usually chosen at greater than twice the bandwidth of the envelope signals (based on the Nyquist theorem). The stimulation pulses are applied in a strictly non-overlapping sequence. Thus, as a typical CIS-feature, only one electrode channel is active at a time and the overall stimulation rate is comparatively high. For example, assuming an overall stimulation rate of 18 kpps and a 12 channel filter bank, the stimulation rate per channel is 1.5 kpps. Such a stimulation rate per channel usually is sufficient for adequate temporal representation of the envelope signal. The maximum overall stimulation rate is limited by the minimum phase duration per pulse. The phase duration cannot be arbitrarily short because, the shorter the pulses, the higher the current amplitudes have to be to elicit action potentials in neurons, and current amplitudes are limited for various practical reasons. For an overall stimulation rate of 18 kpps, the phase duration is 27 μs, which is near the lower limit.

The Fine Structure Processing (FSP) strategy by Med-El uses CIS in higher frequency channels, and uses fine structure information present in the band pass signals in the lower frequency, more apical electrode channels. In FSP, the fine time structure of low frequency channels is transmitted through Channel Specific Sampling Sequences (CSSS) that start at negative to positive zero crossings of the respective band pass filter output (see U.S. Pat. No. 6,594,525, which is incorporated herein by reference). The basic idea of FSP is to apply a stimulation pattern, where a particular relationship to the center frequencies of the filter channels is preserved, i.e., the center frequencies are represented in the temporal waveforms of the stimulation patterns, and are not fully removed, as is done in CIS. Each stimulation channel is associated with a particular CSSS, which is a sequence of ultra-high-rate biphasic pulses (typically 5-10 kpps). Each CSSS has a distinct length (number of pulses) and distinct amplitude distribution. The length of a CSSS may be derived, for example, from the center frequency of the associated band pass filter. A CSSS associated with a lower filter channel is longer than a CSSS associated with a higher filter channel. For example, it may be one half of the period of the center frequency. The amplitude distribution may be adjusted to patient specific requirements. Typically CSSS sequences are applied on up to 3 of the most apical electrode channels, covering the frequency range up to 200 or 330 Hz. The FSP arrangement is described further in Hochmair I, Nopp P, Jolly C, Schmidt M, Schößer H, Garnham C, Anderson I, *MED-EL Cochlear Implants: State of the Art and a Glimpse into the Future*, Trends in Amplification, vol. 10, 201-219, 2006, which is incorporated herein by reference.

For illustration, FIG. 2A-2B show two examples of CSSS for a 6-channel system. In FIG. 2A, the CSSS's are derived by sampling one half of a period of a sinusoid whose frequency is equal to the center frequency of the band pass filter (center frequencies at 440 Hz, 696 Hz, 1103 Hz, 1745 Hz, 2762 Hz, and 4372 Hz). Sampling is achieved by means of biphasic pulses at a rate of 10 kpps and a phase duration of 25 μs. For Channels 5 and 6, one half of a period of the center frequencies is too short to give space for more than one stimulation pulse, i.e., the "sequences" consist of only one pulse, respectively. Other amplitude distributions may be utilized. For example, in FIG. 2B, the sequences are derived by sampling one quarter of a sinusoid with a frequency, which is half the center frequency of the band pass filters. These CSSS's have about the same durations as the CSSS's in FIG. 2A, respectively, but the amplitude distribution is monotonically increasing. Such monotonic distributions might be advantageous, because each pulse of the sequence can theoretically stimulate neurons at sites which cannot be reached by its predecessors.

FIG. 3 illustrates a typical signal processing implementation of the FSP coding strategy. A Band Pass Filter Bank 301 processes an input sound signal to generate spectral band pass signals that each represent a band pass channel defined by an associated band of audio frequencies. Each of these spectral band pass signals is then further processed by a zero crossing detector 303 that detects the negative to positive zeros crossings of each spectral band. The CSSS 305 are inserted at the start of the negative to positive zero crossings of their respective band pass filter output. An envelope detector 307 provides the envelopes of band pass time signals, which include unresolved harmonics and are modulated with the difference tones of the harmonics, mainly the fundamental frequency F0. When the CSSS stimulation pulses are weighted with these envelopes by non-linear mapping module 309, the resulting pulses are undesirably amplitude modulated mainly with F0. This also applies to the frequency bands that are designed to transmit fine time structure, in addition to amplitude cues.

The FS4 coding strategy differs from FSP in that up to 4 apical channels can have their fine structure information used. In FS4-p, stimulation pulse sequences can be delivered in parallel on any 2 of the 4 FSP electrode channels. With the FSP and FS4 coding strategies, the fine structure information is the instantaneous frequency information of a given electrode channel, which may provide users with an improved hearing sensation, better speech understanding and enhanced perceptual audio quality. See, e.g., U.S. Pat. No. 7,561,709; Lorens et al. "Fine structure processing improves speech perception as well as objective and subjective benefits in pediatric MED-EL COMBI 40+ users." *International journal of pediatric otorhinolaryngology* 74.12 (2010): 1372-1378; and Vermeire et al., "Better speech recognition in noise with the fine structure processing coding strategy." *ORL* 72.6 (2010): 305-311; all of which are incorporated herein by reference in their entireties.

FSP and FS4 are the sole commercially available coding strategies that code the temporal fine structure information. Although they have be shown to perform significantly better than e.g. CIS in many hearing situations, there are some other hearing situations in which no significant benefit has been found so far over CIS-like envelope-only coding strategies, in particular with regard to localization and speech understanding in noisy and reverberant conditions.

Temporal fine structure might be more affected by noise than the envelope is. It might be beneficial to use fine structure stimulation depending, for example, on the signal of noise ratio or on the dynamic reverberation ratio. In existing coding strategies, the use of the temporal fine structure is adapted in a post-surgical fitting session and is not adaptive to the signal to noise ratio.

In addition to the specific processing and coding approaches discussed above, different specific pulse stimulation modes are possible to deliver the stimulation pulses with specific electrodes—i.e. mono-polar, bi-polar, tri-polar, multi-polar, and phased-array stimulation. And there also are different stimulation pulse shapes—i.e. biphasic, symmetric triphasic, asymmetric triphasic pulses, or asymmetric pulse shapes. These various pulse stimulation modes and pulse shapes each provide different benefits; for example, higher tonotopic selectivity, smaller electrical thresholds, higher electric dynamic range, less unwanted side-effects such as facial nerve stimulation, etc.

Binaural stimulation has long been used in hearing aids, but it has only recently become common in hearing implants such as cochlear implants (CI). For cochlear implants, binaural stimulation requires a bilateral implant system with two implanted electrode arrays, one in each ear. The incoming left and right side acoustic signals are similar to those in hearing aids and may simply be the output signals of microphones located in the vicinity of the left and right ear, respectively.

Bilateral cochlear implants provide the benefits of two-sided hearing which can allow a listener to localize sources of sound in the horizontal plane. That requires information from both ears such as interaural level differences (ILDs) and interaural time differences (ITDs). This is discussed further, for example, in Macpherson, E. A, and Middlebrooks, J. C., *Listener Weighting Of Cues For Lateral Angle: The Duplex Theory Of Sound Localization Revisited*, J. Acoust. Soc. Am. 111, 2219-3622, 2002, which is incorporated herein by reference. An ITD is a relative time shift between signals arriving at the left and right ear which is caused by different times for the signal to reach each ear when the source of sound is not within the median plane. An ILD is a similar difference in sound levels of signals entering the ears. Two-sided hearing also is known to make speech easier to understand in noise, and again the perception of ITD plays a pivotal role therein. This is explained more fully, for example, in Bronkhorst, A. W., and Plomp, R., *The Effect Of Head-Induced Interaural Time And Level Differences On Speech Intelligibility In Noise*, J. Acoust. Soc. Am. 83, 1508-1516, 1988, which is incorporated herein by reference.

Complex room sound situations (e.g. echoes) impede sound localization performance in bilateral cochlear implant systems. The room acoustic signals that arrive at a listener's two ears are characterized by a change in interaural coherence (e.g., Faller et al., "Source localization in complex listening situations: Selection of binaural cues based on interaural coherence," *The Journal of the Acoustical Society of America* 116.5 (2004): 3075-3089; incorporated herein by reference in its entirety). The onset of a sound emitted from a nearby sound source may have a high interaural correlation, whereas later sound components may be overlaid by echoes from different directions and may show little or no interaural correlation.

Basic psychoacoustic experiments (Monaghan et al., "Factors affecting the use of envelope interaural time differences in reverberation," *The Journal of the Acoustical Society of America* 133.4 (2013): 2288-2300; incorporated herein by reference in its entirety) have shown that the access to signal components with high interaural correlation may be beneficial to stream segregation in the normal-hearing. But existing bilateral cochlear implant systems do not implement methods to enhance sound localization performance.

U.S. Patent Publication 20080319509 describes a method to improve ITD perception which reduces periodic characteristics of the signal. Single coding strategy concepts such as the FS4 strategy are able to code ITDs if the latter are present in the corresponding band-pass signals (see U.S. Pat. No. 8,798,758 and U.S. Pat. No. 7,283,876, both of which are incorporated herein by reference in their entireties). Other stimulation concepts also have been shown to transmit ITDs, for example using peak-derived timing as described in U.S. Pat. No. 7,310,558, which is incorporated herein by reference in its entirety. Nevertheless, none of the known described implementations considers that ITDs might be smeared by the presence of echo or other disturbing secondary sound sources, and therefore they code both valid and invalid ITDs with equal weight.

SUMMARY

Embodiments of the present invention are directed to systems and methods for signal processing in a bilateral hearing implant system having left side and right side hearing implants. At least one sensing microphone for each hearing implant is configured for sensing a sound environment for that hearing implant to develop a corresponding microphone signal output. A filter bank for each hearing implant is configured for processing the microphone signal to generate a plurality of band pass signals for that hearing implant, wherein each band pass signal represents an associated band of audio frequencies. An interaural coherence analysis module is configured to receive input signals from each hearing implant including the microphone signals and the band pass signals, and is configured to analyze the input signals to produce an interaural coherence signal output characterizing reverberation-related similarity of the input signals. A pulse timing and coding module for each hearing implant is configured for processing the band pass signals to develop stimulation timing signals, wherein for one or more selected band pass signals, wherein the processing includes using an envelope gating function developed from the interaural coherence signal. A pulse generation module for each hearing implant is configured for processing the stimulation timing signals to develop electrode stimulation signals for the hearing implant for perception as sound.

In further specific embodiments, the envelope gating function may be configured to modify band pass envelope components of the band pass signals to produce gated envelopes that are applied to the stimulation timing signals. For example, the gating function may use a gating threshold value such that when a band pass envelope is greater than or equal to the gating threshold value, the gated envelope equals the band pass envelope, and when a band pass envelope is less than the gating threshold value, the gated envelope is zero. Or the gating function may be configured to produce variable amplitude gated envelopes that increase in amplitude as the gating function increases in amplitude.

The pulse stimulation and timing module may be configured to use Continuous Interleaved Sampling (CIS) and/or Channel Specific Sampling Sequences (CSSS) to develop the electrode stimulation signals. The interaural coherence module may be configured to select one or more of the input signals to analyze using a switching arrangement controlled as a function of Auditory Scene Analysis (ASA), or based on a configurable input switch set during a user fitting process.

DETAILED DESCRIPTION

Parameters of a given cochlear implant signal coding strategy might not be optimal for all listening conditions. For example, in noisy conditions some coding strategies might perform better than others since temporal fine structure typically is more affected by noise than is the band pass signal envelope. It would be beneficial to switch from one coding strategy to another, depending on listening conditions. The switching could be performed in small increments so that the transition happens in a smooth morphing from one coding strategy to the other. The audio input signal is monitored and analyzed to estimate one or more key features that are present. Based on the key feature(s), the signal coding strategy is automatically modified.

As an example of a key feature, the signal to noise ratio (SNR) of the audio input signal can be estimated. It is assumed that event-based coding strategies that transmit temporal fine structure of the input signal (such as FSP by MED-EL) are optimal in relatively quiet listening conditions, while envelope-based coding strategies (such as HD-CIS by MED-EL are better in noisier conditions. A smooth transition can then be made automatically from FSP to HD-CIS based on the SNR of the audio input signal by modifying the length and the shape of the channel-specific sampling sequences (CSSS) that are used for the output stimulation pulses.

Figure 1:
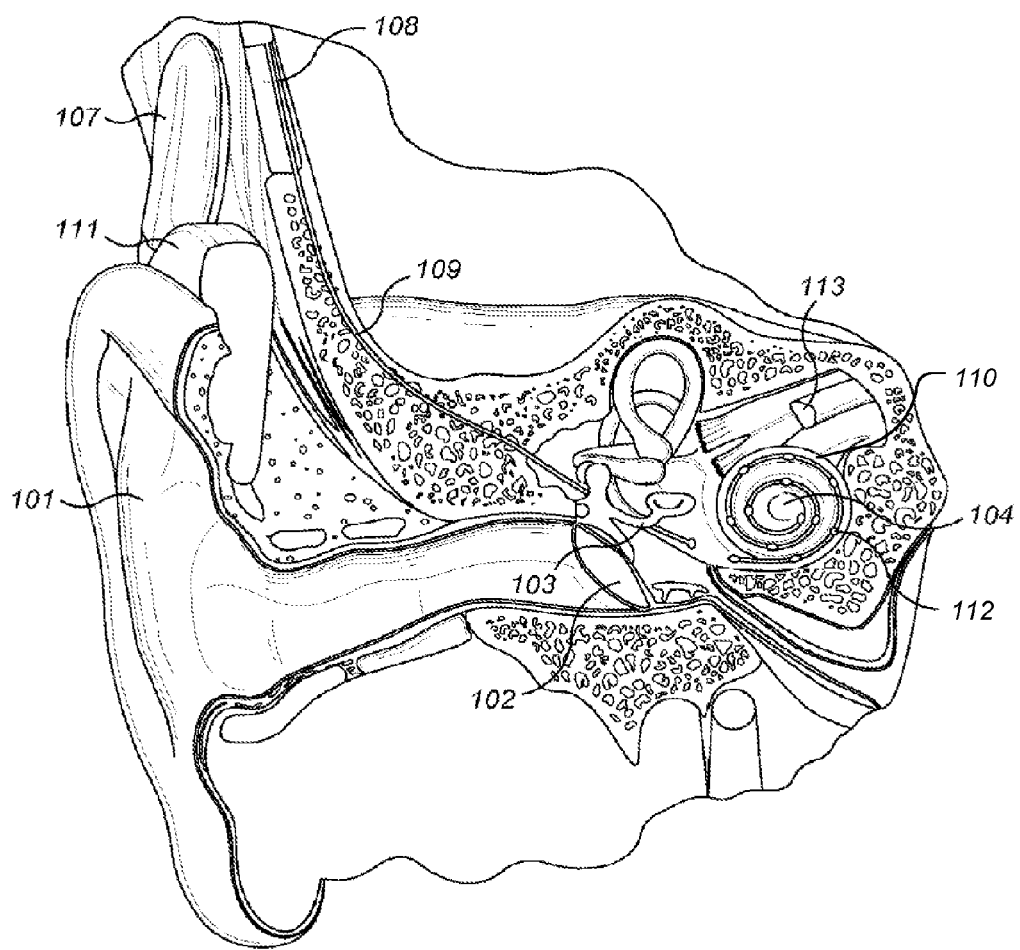
FIG. 1 shows anatomical structures of a human ear and some components of a typical cochlear implant system.
Figure 2A:
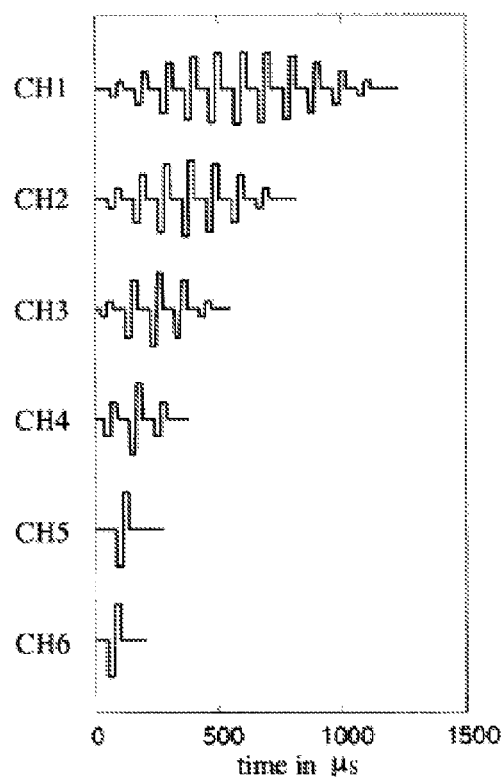
FIGS. 2A and 2B show channel specific sampling sequences (CSSS) for two 6-channel systems utilizing biphasic pulses at 10 kpp/s and phase duration of 25 μs.
Figure 2B:
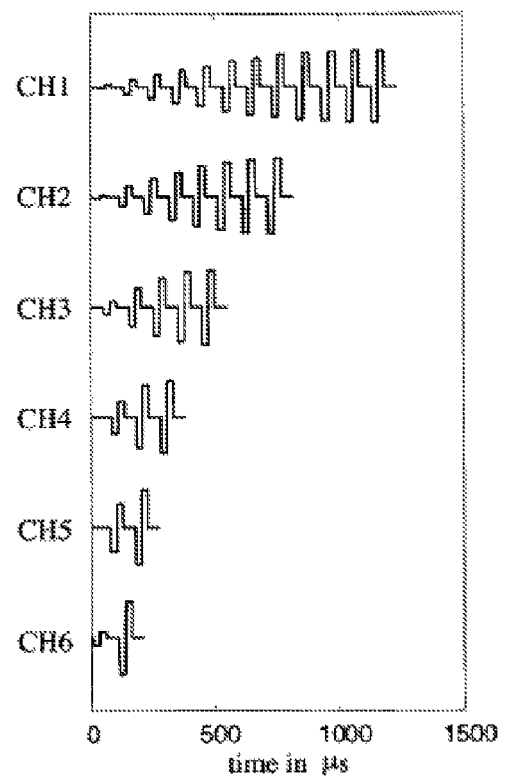
Figure 3:
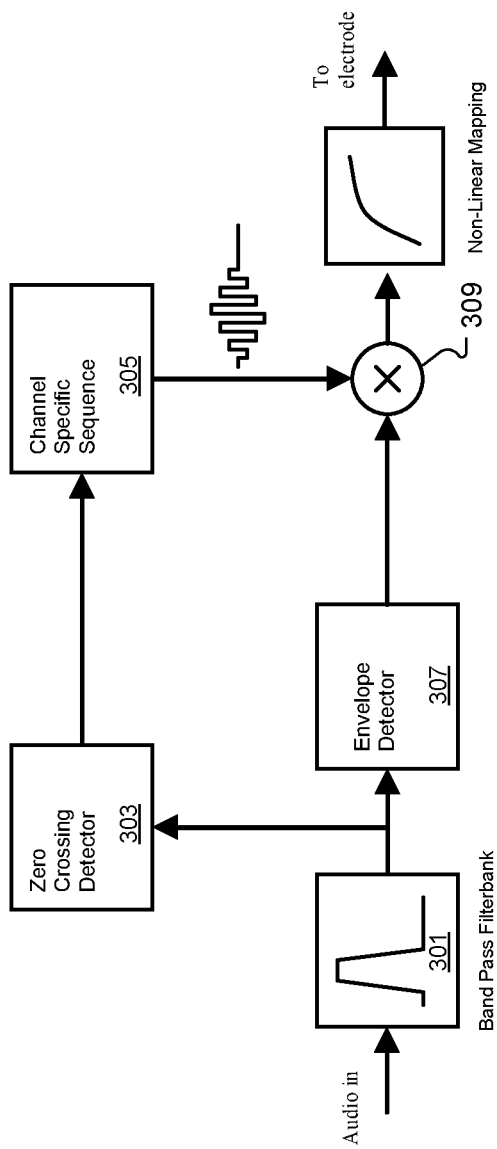
FIG. 3 shows various functional blocks in a prior art fine structure processing (FSP) signal processing arrangement.
Figure 4:
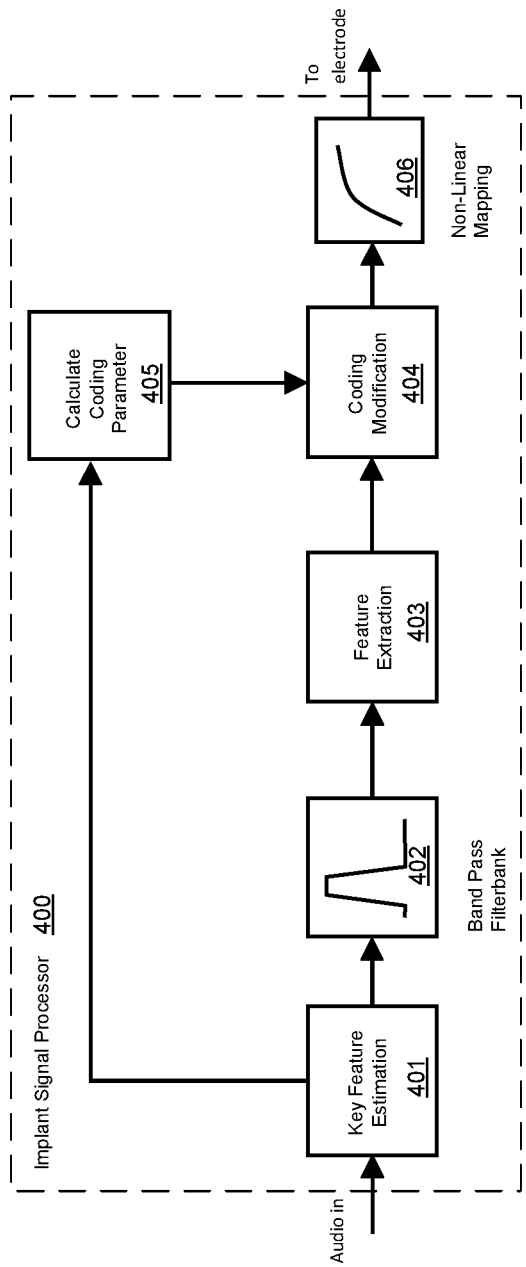
FIG. 4 shows various functional blocks in a coding modification signal processing arrangement according to an embodiment of the present invention.

FIG. 4 shows various functional blocks in a generic coding modification signal processing arrangement for a hearing implant system that has an implanted electrode array with multiple stimulation contacts for delivering electrode stimulation signals to adjacent auditory neural tissue. The implant signal processor 400 uses an FSP approach and includes a key feature estimation module 401 that monitors one or more key features in an audio input signal that reflects the current hearing environment. A conventional band pass filter bank 402 processes the audio input signal to generate multiple band pass signals which each represent associated bands of audio frequencies in the audio input signal.

A feature extraction module 403 processes the band pass signals from the band pass filter bank 402 to extract the band pass envelopes and fine structure time information and generate an initial set of stimulation pulses for the stimulation contacts according to an original coding strategy. For example, the original coding strategy may be an event-based coding strategy such as FSP that uses adaptive stimulation rates according to the fine structure information in the band pass signals.

A coding parameter module 405 monitors the key feature from the key feature estimation module 401 and so long as value of the key feature is less than or equal to some given initial value, the coding modification block 404 passes along the stimulation pulses as produced by the feature extraction module 403 according to the original coding strategy. At some point when the key feature is greater than or equal to a coding change value, the coding parameter module 405 controls the coding modification block 404 to begin adjusting the stimulation pulses to adaptively change the original coding strategy over a transition period of time to automatically transition to the new coding strategy. For example, the new coding strategy may be an envelope-based coding strategy such as CIS or HD-CIS that uses stimulation pulses at a constant stimulation rate. The implant signal processor 400 may specifically be configured for automatically transitioning either while the key feature changes from the initial value to the coding change value, or after. A non-linear mapping module 406 then adjusts the amplitude of the output stimulation pulses using anon-linear mapping that provides patient-specific scaling and data stream generation.

Figure 5:
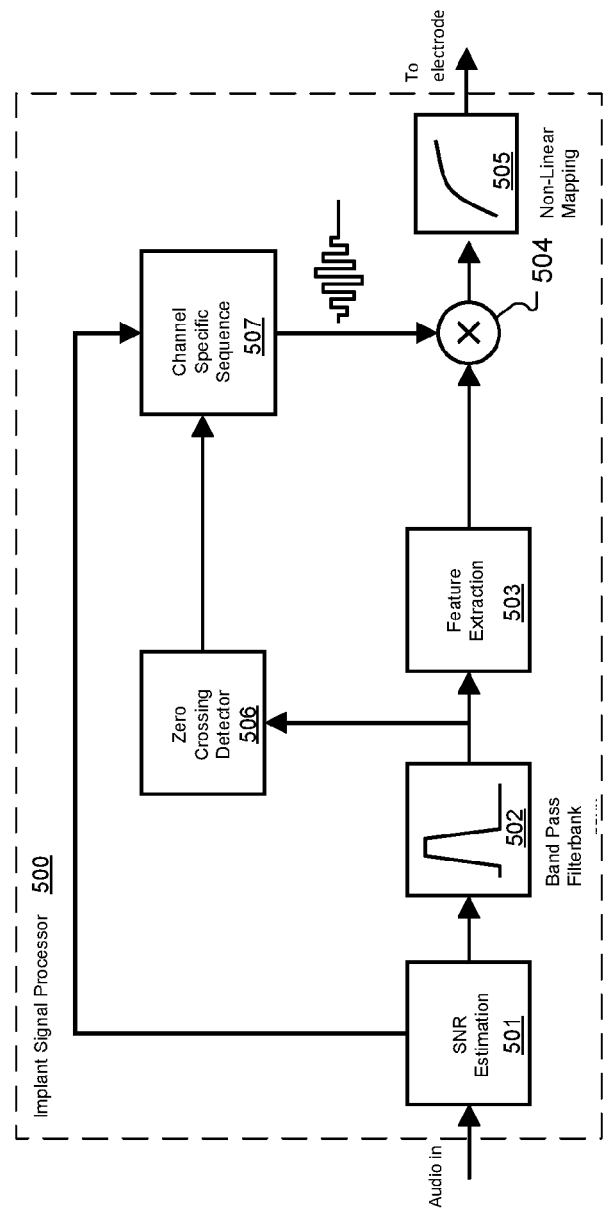
FIG. 5 shows various functional blocks in a specific embodiment of the present invention using SNR as the key feature with CSSS.

FIG. 5 shows various functional blocks in an embodiment of the present invention where the implant signal processor 500 uses SNR as the key feature with CSSS pulse sequences. An SNR estimation module 501 that monitors one or more key features in the input signal, while a band pass filter bank 502 processes the audio input signal to generate the band pass signals. A zero crossing detector 506 detects the negative to positive zeros crossings of each band pass signal (the temporal fine structure information). A channel specific sequence module 507 creates CSSS output timing request pulses at the start of the negative to positive zero crossings of each band pass signal, while a feature extraction module 503 derives the band pass signal envelopes. The pulse weighting module 504 weights (amplitude modulates) the CSSS stimulation pulses with the band pass envelopes, which is then further adjusted by the non-linear mapping module 505 that provides patient-specific scaling and data stream generation.

At each zero crossing trigger event from the zero crossing detector 506, the channel specific sequence module 507 determines an event-specific length for the CSSS pulse sequence ("FL interval"). The pulse weighting module 504 shapes the CSSS pulse sequence to follow the band pass envelope amplitude so that the band pass envelope is sampled with the CSSS sequence. When the SNR signal from the SNR estimation module 501 is relatively high (quiet sound environment), the channel specific sequence module 507 adjusts the FL interval to be so short that a CSSS pulse sequence may consist of as little as a single pulse. As the SNR signal from the SNR estimation module 501 decreases (the environment becomes noisier), the channel specific sequence module 507 increases the FL interval and adds more pulses to the CSSS sequence until at some point for a low SNR (high noise), the last pulse of the CSSS sequence is seamlessly followed by the first pulse of the next CSSS sequence, resulting in a continuous (constant rate) sampling of the band pass envelopes from the feature extraction module 503. If the length of the FL interval becomes larger than the time between two consecutive trigger events (i.e., two zero crossings), the channel specific sequence module 507 may terminate the existing CSSS sequence when the next trigger event occurs and the FL interval of the following trigger event overrules the previous FL interval. Or the channel specific sequence module 507 may continue with the CSSS pulse sequence initiated by the first trigger event and ignore the subsequent trigger event so that the end of the existing FL interval, a new FL interval is determined. Once the SNR signal from the SNR estimation module 501 increases again, the channel specific sequence module 507 adaptively adjusts the FS interval to again become shorter than the times between the trigger events.

Figure 6:
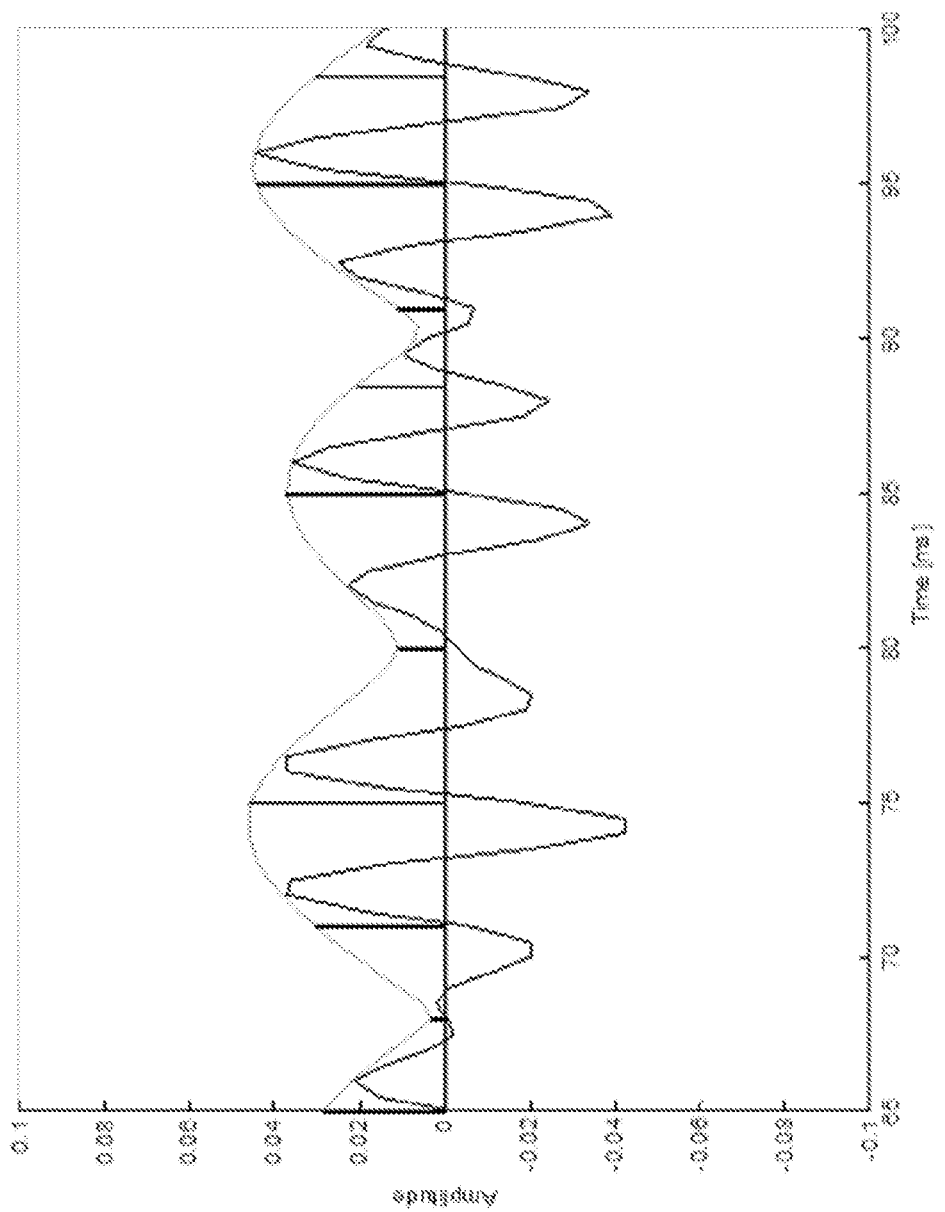
FIG. 6 shows an example of a processed band pass signal and the resulting CSSS pulse sequence for a vowel with added Gaussian noise and a SNR=10 dB.
Figure 7:
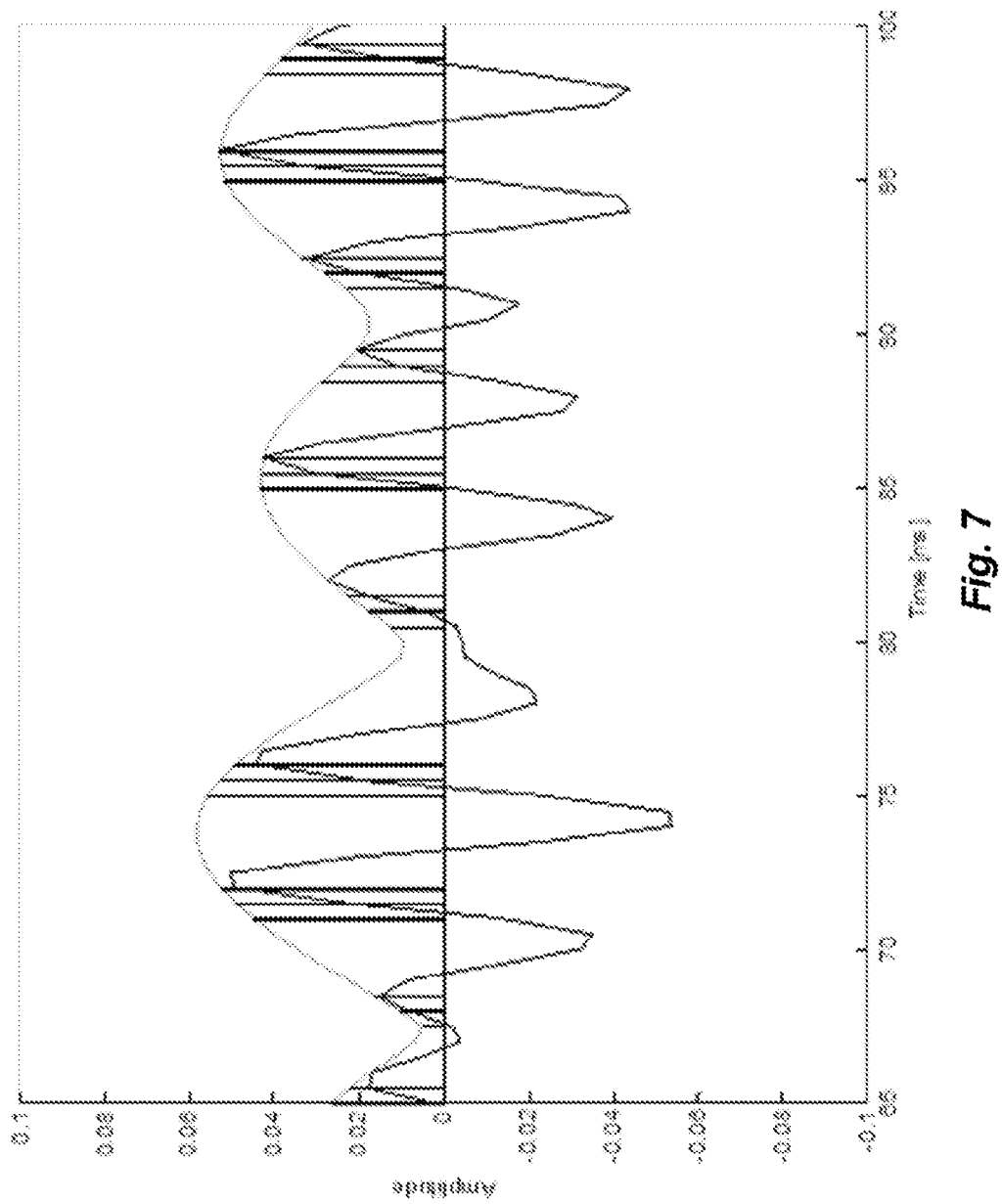
FIG. 7 shows the same signal as in FIG. 6, with SNR=5 dB.
Figure 8:
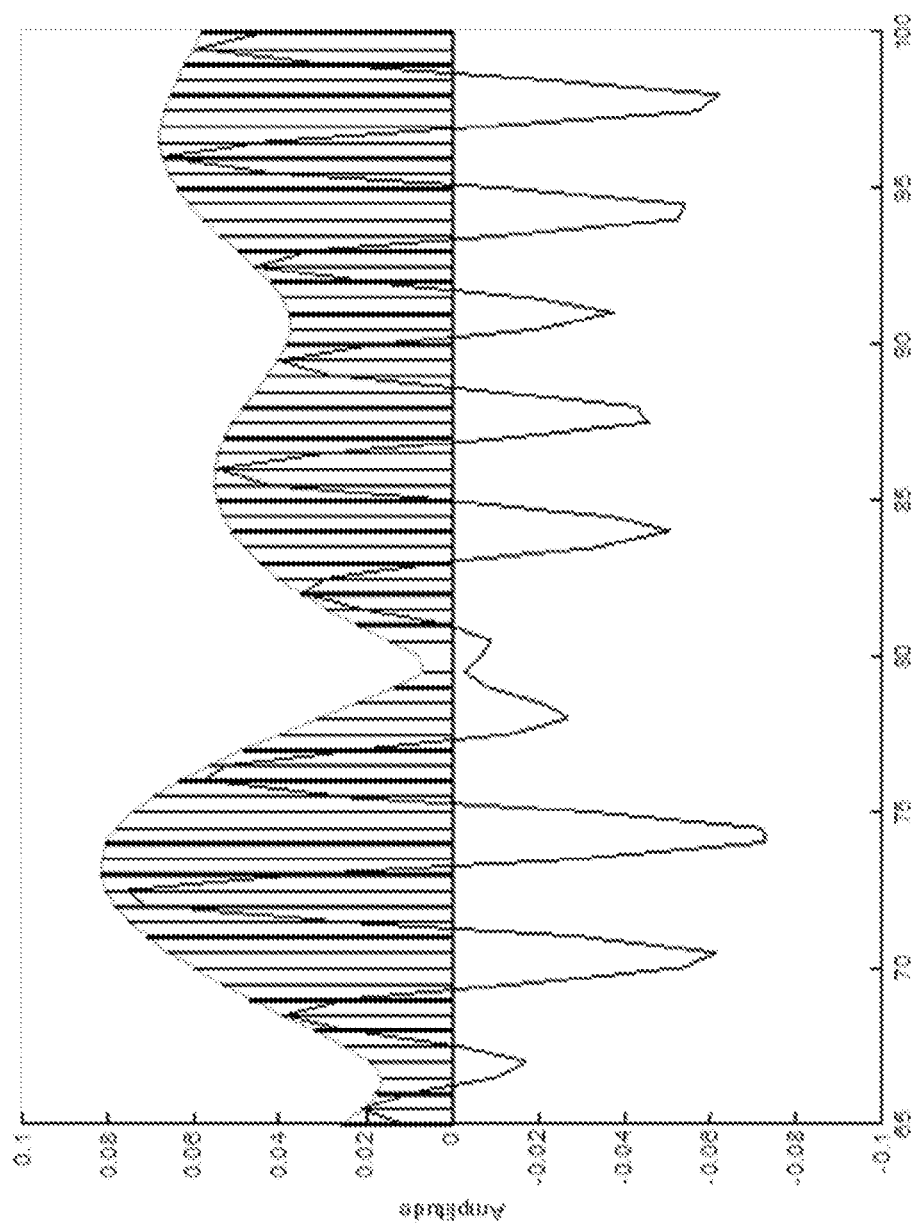
FIG. 8 shows the same signal as in FIG. 6, with SNR=0 dB.

FIG. 6 shows an example of a processed band pass signal and the resulting CSSS pulse sequence for a vowel with added Gaussian noise and a SNR=10 dB. The band pass signal is the higher frequency full sine wave signal in dark gray, the Hilbert band pass envelope is the slower varying half sine wave trace shown in light gray, and the vertical black lines represent the applied CSSS sequences with a sequence length of one. FIG. 7 shows the same signal as in FIG. 6, when the SNR signal decreases down to 5 dB (more noise) and the FL interval is increased so that the CSSS sequences contain three pulses each. FIG. 8 shows the same signal as in FIG. 6, with SNR=0 dB (noisier still) where the FL interval is so long that the CSSS sequence performs a continuous sampling of the band pass envelope that is similar to the HD-CIS coding strategy.

In addition to or alternatively to adaptively varying the length of the CSSS interval, other specific embodiments may adaptively control other signal variables. For example, in combination with the application of a CSSS pulse at a specific event (e.g. a zero crossing event), a subsequent time interval—FS-interval—may be determined within which a pulse has to be applied. The length of this FS-interval may be determined by the value of the SNR signal at the time when the pulse has been applied: If the SNR is high, the FS-interval may be chosen to be long, while if the SNR is low, the FS-interval may be chosen to be short. To restrict the stimulation rate to a maximum value that reflects the refractory period of the auditory nerve fibers, a shortest possible FS-interval can be defined that corresponds to the maximum stimulation rate. There are several different specific possibilities:

If another timing event occurs within the FS-interval determined from the previous timing event, and the time between the two timing events is greater than the refractory period, then a pulse can be applied at the second timing event and a new FS-interval is initiated that overrules the previous one.

If another timing event occurs within the FS-interval determined from the previous timing event, but the time between the two timing events is shorter than the refractory period, then a pulse can be applied at the end of the refractory period and a new FS-interval is initiated that overrules the previous one.

If no additional timing event appears before the end of the current FS-interval and the refractory period is shorter than the FS-interval, then another pulse can be applied (forced) at the end of the FS-interval.

If no additional timing event appears before the end of the current FS-interval interval, but the refractory period is greater than the FS-interval, then another pulse can be applied (forced) at the end of the refractory period.

In general, an embodiment may require that a subsequent pulse (either caused by the occurrence of a timing event or by the end of the FS-interval) can only be applied if a minimum period (e.g. the refractory period) is over. In some applications, it may be advantageous to have a shorter period than the refractory period as the minimum period.

Figure 9:
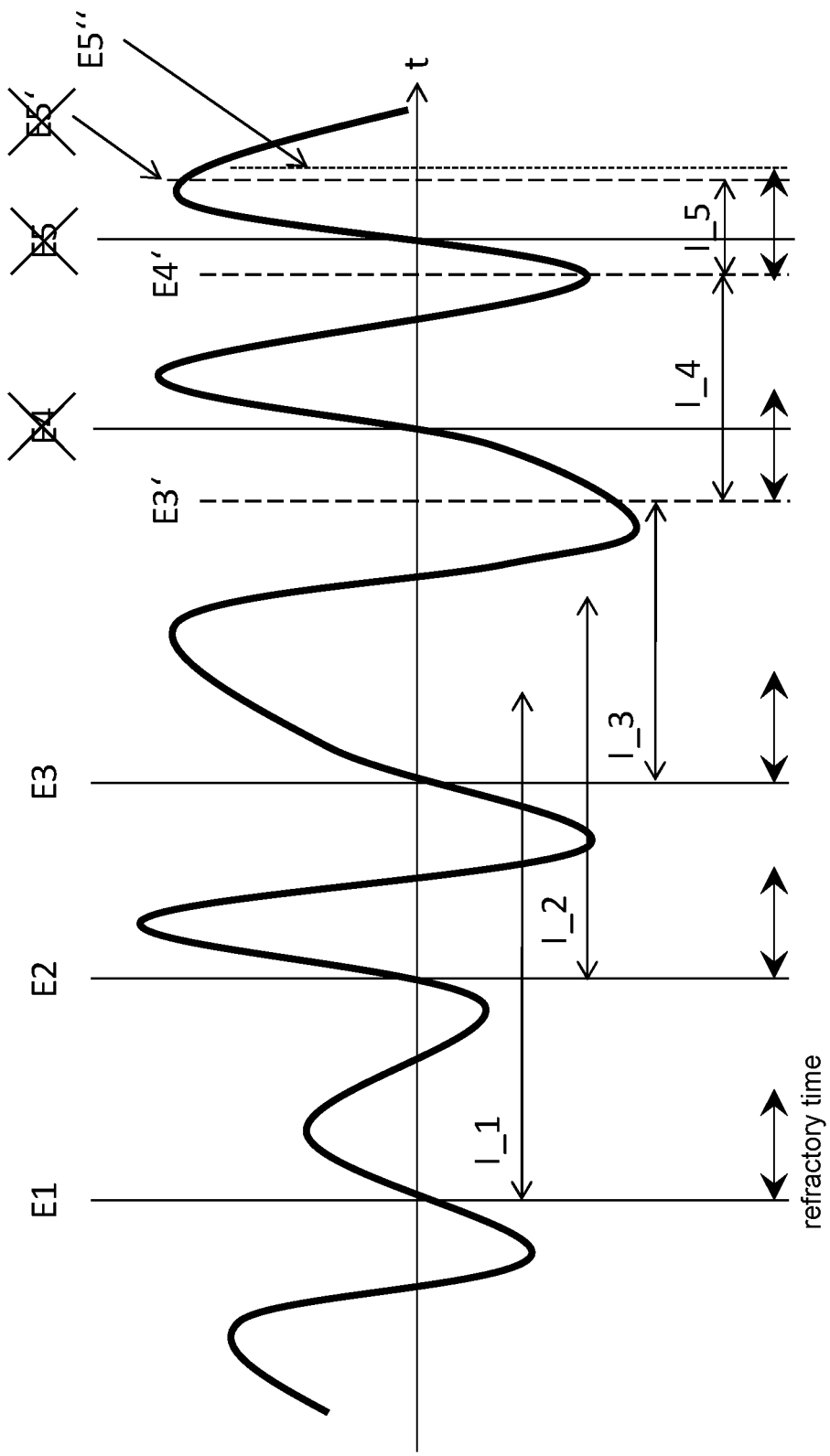
FIG. 9 shows an example of a processed band pass signal and SNR-adapted pulse time intervals according to an embodiment of the present invention.

FIG. 9 shows an example of a processed band pass signal and SNR-adapted pulse time intervals according to an embodiment of the present invention. In FIG. 9, it is assumed that five zero crossing timing events E1-E5 (vertical solid lines) are detected, the SNR is decreasing over time t (i.e. from left to right), and the refractory period is as shown by the corresponding horizontal arrows across the bottom the figure denoted as "refractory time". The first CSSS pulse is, without limitation, applied at the zero crossing event E1. Since the SNR is high, the corresponding FS-interval I_1 is relatively long. The next zero crossing event E2 occurs before the end of the I_1 FS-interval, so the next CSSS pulse is applied at E2, and the same situation with I_2 and E3 although the SNR has meantime decreased so that I_2 is shorter than I_1. However, at the event E3' that occurs at the end of the I_3 FS-interval, a CSSS pulse is forced because no further zero crossing has occurred within this FS-interval starting after zero crossing event E3 (also the refractory time (after E3) is still shorter than I_3). The next zero crossing event occurs at E4, but that is still within the refractory period after the last applied pulse at E3' so there is no pulse applied at E4 nor is any corresponding FS-interval determined. Similarly, at E5 no pulse is applied, and in addition, at E4' the SNR is so low that the corresponding I_5 FS-interval is determined to be shorter than the refractory period so at E5', no pulse is applied but instead is delayed until E5" corresponding to the end of the refractory period after event E4'.

When the SNR later increases more and more (not shown in FIG. 9) the FS-intervals will again become longer and longer until a zero crossing event will be detected after the end of the refractory time but before the end of an FS-interval. From that point on, the zero crossing events will again determine the pulse sequence and the coding strategy follows the known event-based coding strategies until the SNR decreases again. The maximum stimulation rate can be set to be proportional to the inverse of the minimum possible interval (e.g. the refractory period) so that the instantaneous stimulation rate (which equals 1/FS-interval) cannot exceed a given defined value; e.g. a typical rate as presently used for CIS or HD-CIS coding strategies. In general, the lower the SNR, the more the resulting sound coding sequence will be according to an envelope-based coding strategy such as CIS or HD-CIS (constant sampling of each channel in a prescribed manner with the defined maximum stimulation rate). The higher the SNR, the more the resulting sound coding sequence will be like according to a pure event-based coding strategy such as FSP.

The MCL and THR values may vary when switching from one specific coding strategy to another, so the MCL and THR values of the patient-specific scaling function should also be adjusted (in addition to the CSSS sequence) to promote a loudness-balanced transition between the different coding strategies.

The modification of the CSSS sequences can also be done channel-wise, i.e. based on channel-specific SNR values. And while the foregoing was described with SNR being the parameter for subsequent adaptive modifications, other specific signal parameters that characterize the quality of an existing hearing situation may be used as well; e.g. the direct to reverberation ratio (DRR).

Both approaches—variation of CSSS lengths and determination of time intervals within which no pulse is applied—yield similar overall results: a smooth transition between event-based (variable rate) and envelope-based (constant rate) coding strategies. Embodiments of the present invention adapt the sound coding strategy to changes in the sound environment with optimal settings for each environment. With SNR-adjusted sampling, temporal fine structure is provided in situations where it is not disturbed, while the sound coding is morphed seamlessly to a more noise-robust envelope coding for better sound perception in noisier environments.

Another key feature that may be useful for sound localization in a bilateral cochlear implant system is interaural coherence, which is a measure of the similarity of sound waves that reach the two ears of a subject. Interaural coherence is related to reverberation. The first wave front originating from a sound source (e.g. speaker) that reaches the ears is free of reflections and therefore provides high interaural coherence. But succeeding reverberant sound waves have reduced interaural coherence. Interaural coherence can be used as an indicator for the reliability of interaural time delay (ITD) and interaural level difference (ILD) cues for sound localization; see, Faller 2004). Accurate coding of the reflection-free periods can enable more robust sound localization and speech cues.

Band pass envelopes provide robust sound localization cues and ITD thresholds decrease as envelope modulation increases (Laback, Bernhard, et al. "Effects of envelope shape on interaural envelope delay sensitivity in acoustic and electric hearing," *The Journal of the Acoustical Society of America* 130.3 (2011): 1515-1529; incorporated herein by reference in its entirety). This effect may be useful for sharpening the envelope signals during periods of high interaural coherence in the input signals.

Figure 10:
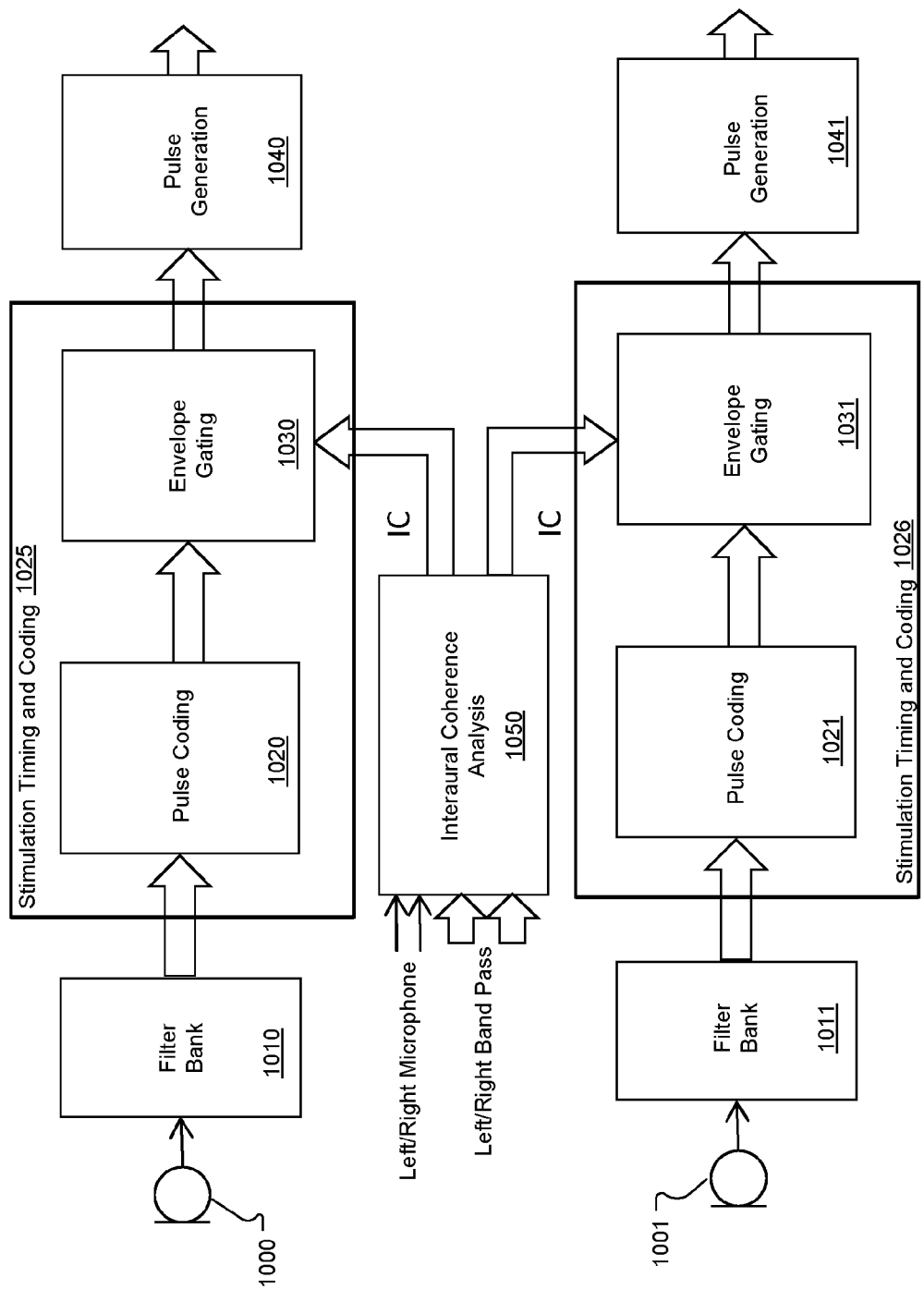
FIG. 10 shows various functional blocks for a signal processing arrangement for a bilateral cochlear implant system that uses an interaural coherence analysis module according to an embodiment of the present invention.
Figure 11:
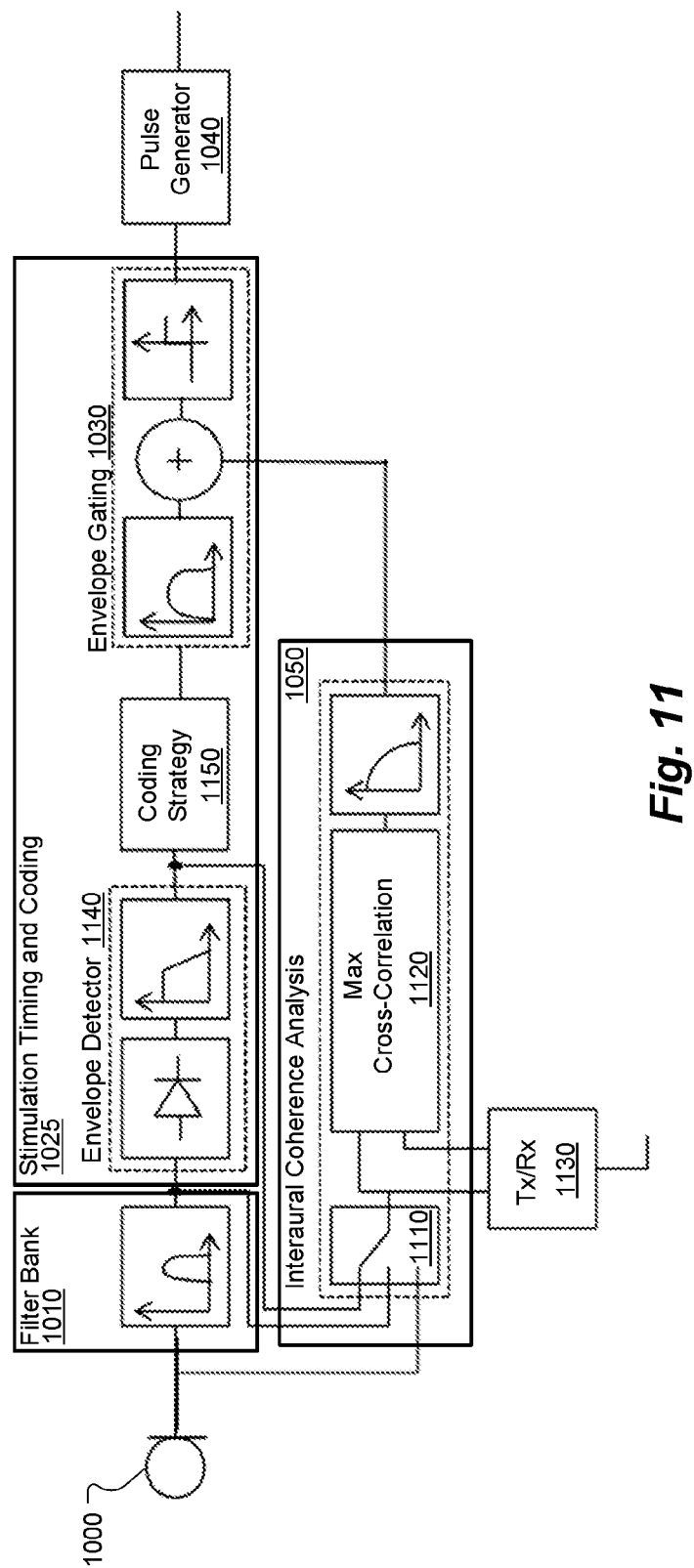
FIG. 11 shows greater functional detail for one side of a bilateral cochlear implant system as shown in FIG. 17.

Therefore, embodiments of the present invention are directed to systems and methods for signal processing in a bilateral hearing implant system based on using interaural coherence in an envelope gating function. FIG. 10 shows various functional blocks for a signal processing arrangement for a bilateral cochlear implant system that uses an interaural coherence analysis module according to an embodiment of the present invention. FIG. 11 shows greater functional detail for one side of a bilateral cochlear implant system as shown in FIG. 10.

At least one sensing microphone 1000 and 1001 for each hearing implant is configured for sensing a sound environment for that hearing implant to develop a corresponding output microphone signal. A filter bank 1010 and 1011 for each hearing implant is configured for processing the microphone signals to generate band pass signals for that hearing implant. Each band pass signal represents an associated band of audio frequencies via characteristic temporal fine structure features and a characteristic band pass envelope reflecting time varying amplitude of the band pass signals. The band pass signals are output by the filter banks 1010 and 1011 to stimulation timing and coding modules 1025 and 1026 develop stimulation timing signals for the pulse generator modules 1040 and 1041 that produce the output stimulation pulse signals to the hearing implants for perception as sound.

At least one interaural coherence analysis module 1050 is configured to receive input signals from each hearing implant including the left/right microphone signals and the left/right band pass signals. The interaural coherence analysis module 1050 is configured to analyze the input signals to output an interaural coherence signal that characterizes reverberation-related similarity of the input signals. For example, the interaural coherence analysis module 1050 can compute the interaural coherence signal as described in Faller 2004 as the maximum value of the normalized cross-correlation function, which then is scaled to lie in the range of [0, 1], where 1 indicates maximum interaural coherence.

In specific embodiments, there may be a single interaural coherence analysis module 1050 that is configured to produce an interaural coherence signal for both hearing implants. For example, a single interaural coherence analysis module 1050 may be located in a remote relay device which is communicatively coupled to both the left side and right side of the bilateral cochlear implant system. In that case, the input signals are transmitted to the remote relay device, which calculates the value of the interaural coherence signal, which then is transmitted back to the stimulation timing and coding modules 1025 and 1026. Or there may specifically be an interaural coherence analysis module 1050 for each hearing implant, in which case the left side and right side are symmetric, and each interaural coherence analysis module 1050 can independently calculate the interaural coherence signals. If communication between the left and right sides (directly or via a remote relay station) is harmed or deactivated, each side implant can continue to operate independently.

Focusing on FIG. 11, the at least one interaural coherence analysis module 1050 may be configured to specifically include a signal switch 1110 that selects one or more of the input signals—the left/right microphone signals and the left/right band pass signals—to provide selected internal input signals into a cross correlation module 1120 that which calculates the cross correlation function of the input signals. The signal switch 1110 may be dynamically controlled (e.g. based on the instantaneous output of an auditory scene analysis (ASA) system configured to identify the sound environment as quiet, speech in noise, no speech, music, etc. . . . ). Or the signal switch 1110 may be set during a user fitting process. The signal switch 1110 should be the same on both left and right sides, and the same input signals should be selected on each side. The contralateral input signal comes to the other side via the Tx/Rx block 1130. Alternatively, in some embodiments there may be no signal switch 1110 and either the input signal(s) may be provided directly to a cross correlation module 1120 (again using the same arrangement on each side of the bilateral system).

The stimulation timing and coding module 1025 (on the left side and 1026 on the right side) is configured for processing the band pass signals using a pulse coding module 1020 (on the left side and 1021 on the right side) and an envelope gating module 1030 (on the left side and 1031 on the right side). The pulse coding module 1020 includes envelope detector 1140 (FIG. 11) that extracts the band pass envelopes using rectification and low-pass filtering and coding strategy module 1150 (FIG. 11) that creates corresponding stimulation timing signals, for example, using envelope-based CIS coding, though other stimulation coding strategies may also be used.

The envelope gating module 1030 is configured for processing the band pass envelopes and the stimulation timing signals from the pulse coding module 1020 by applying an envelope gating function based on the interaural coherence signal from the at least one interaural coherence analysis module 1050 to output the stimulation timing signals to the pulse generator 1040 for output as stimulation pulses for the hearing implant for perception as sound. For example, the envelope gating module 1030 can perform envelope gating by filtering the band pass envelope and using this band pass filtered envelope as gating function: if the gating function is greater than some gating threshold thr_gate, then the gated envelope env_gated equals the original envelope. For other values of the gating function, env_gated is set to zero. The stimulation pulses are then weighted with the gated envelope, env_gated.

A further specific embodiment could use the magnitude of the interaural coherence signal to control envelope sharpening. The extent to which the envelope is sharpened (e.g. the amount of envelope gating) can be controlled, for example, via variation of the gating threshold thr_gate: The smaller thr_gate, the less stimulation pulses will be affected by the gating algorithm. The gating threshold thr_gate could be computed with a scaling factor alpha e.g. by:

gating_thr=(1−IC)/alpha;

The gated envelope env_gated is then derived from the envelope env and a band pass filtering function filter by:

```
env_filt = filter(env)
if env_filt < gating_thr then
env_gated = 0
else
env_gated = env;
```

Stimulation pulses are weighted then with the gated envelope env_gated.

Figure 12:
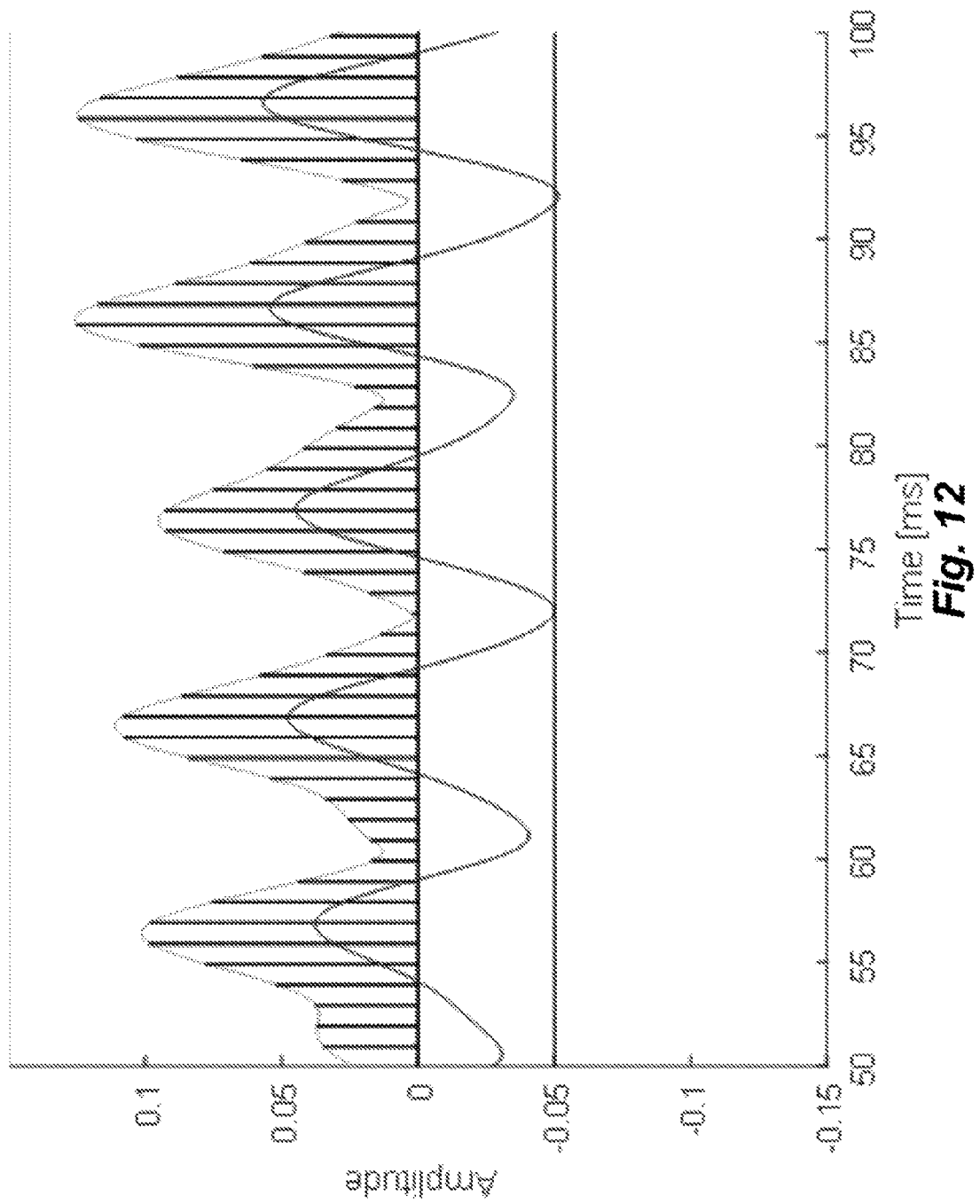
FIG. 12 shows an example waveform for signal processing according to the invention when interaural coherence equals zero.

FIG. 12 shows an example of envelope gating with low interaural coherence (IC=0), where no envelope gating is applied. The figure shows the envelope signal, the gating signal and stimulation pulses in a stimulation channel with the frequency range from 500 to 700 Hz. The gating signal is derived by band pass filtering of the envelope signal with lower cutoff frequency of 100 Hz and an upper cutoff frequency of 300 Hz. The input signal is a speech sample of the sound "aba". The horizontal line parallel to the x-axis indicates the gating threshold gating_thr. Because the filtered envelope signal is always above the gating threshold, envelope gating is never performed.

Figure 13:
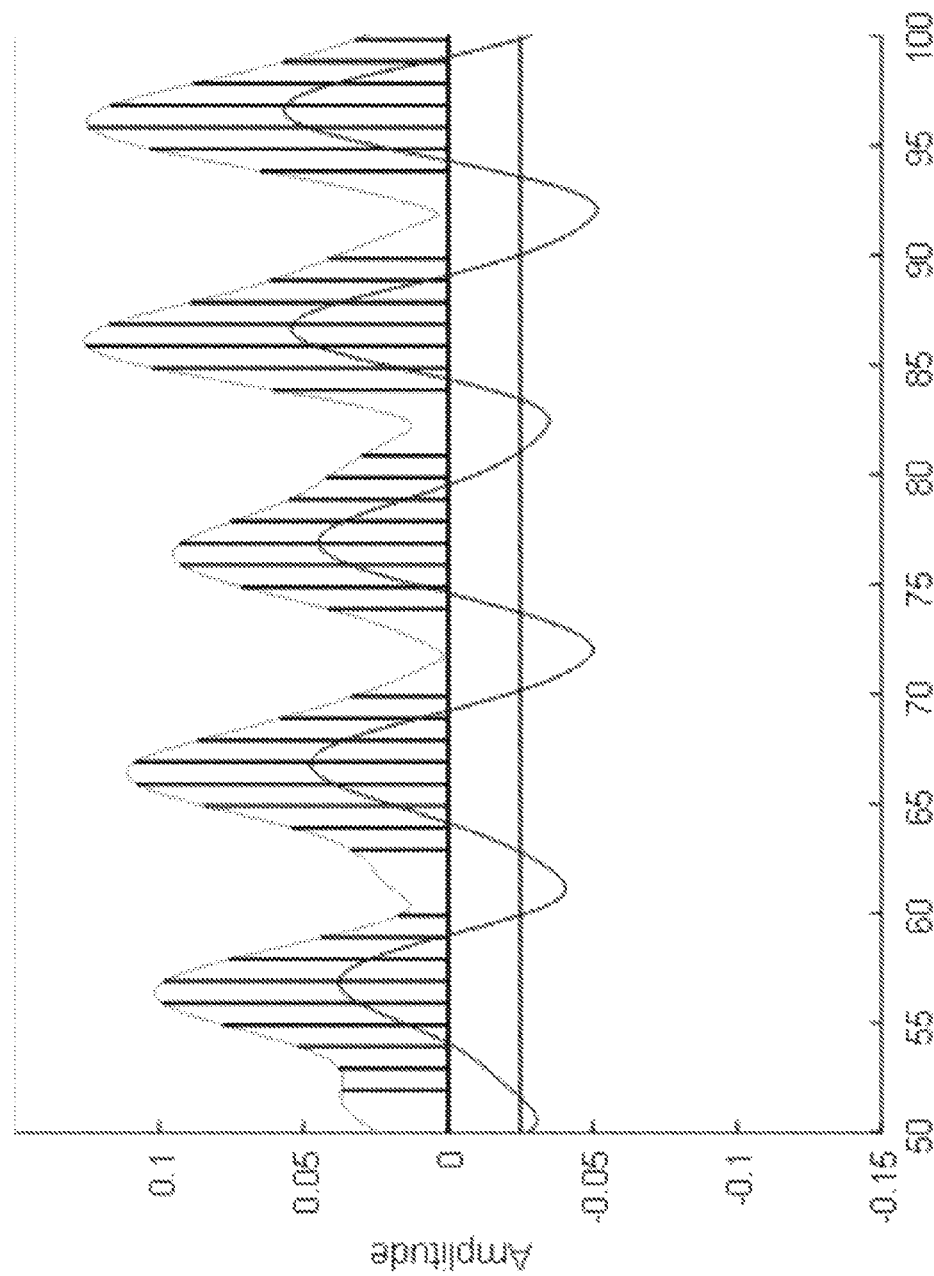
FIG. 13 shows an example waveform for signal processing according to the invention when interaural coherence equals 0.5.

FIG. 13 shows another example of envelope gating with medium interaural coherence (IC=0.5), where a moderate envelope gating is applied. The gating threshold is shown and envelope gating is performed at times where the filtered envelope signal is below the gating threshold. Therefore, relatively few pulses with low envelope values are affected by the gating function.

Figure 14:
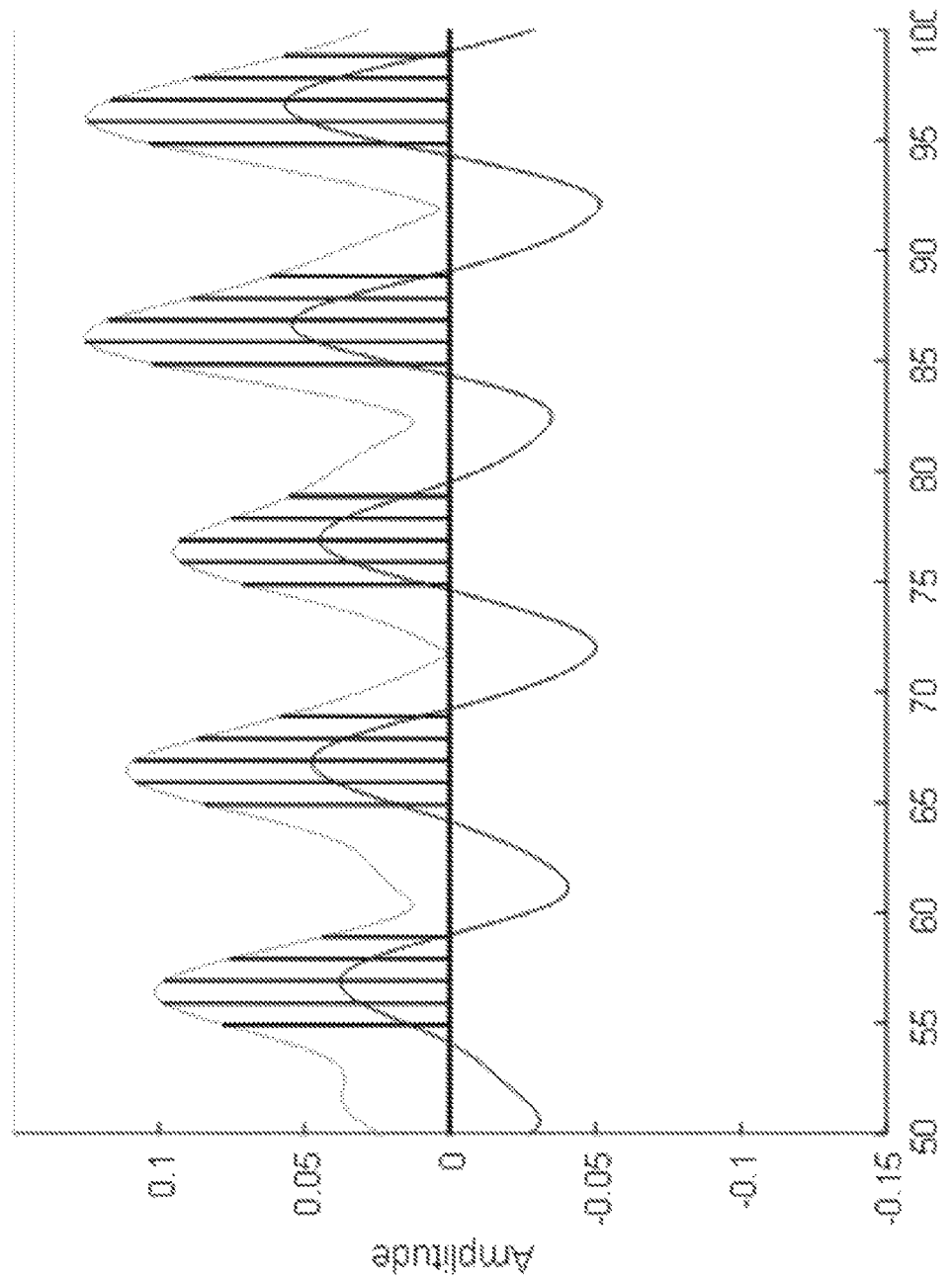
FIG. 14 shows an example waveform for signal processing according to the invention when interaural coherence equals one.

FIG. 14 shows the outcome of envelope gating with high interaural coherence (IC=1), where maximum envelope gating is applied. The gating threshold is zero in this example and timing pulses are only applied at times where the filtered envelope signal is greater than the gating threshold. Only timing pulses with high envelope values are not affected by the gating function.

Embodiments of the invention may be implemented in part in any conventional computer programming language such as VHDL, SystemC, Verilog, ASM, etc. Alternative embodiments of the invention may be implemented as pre-programmed hardware elements, other related components, or as a combination of hardware and software components.

Embodiments can be implemented in part as a computer program product for use with a computer system. Such implementation may include a series of computer instructions fixed either on a tangible medium, such as a computer readable medium (e.g., a diskette, CD-ROM, ROM, or fixed disk) or transmittable to a computer system, via a modem or other interface device, such as a communications adapter connected to a network over a medium. The medium may be either a tangible medium (e.g., optical or analog communications lines) or a medium implemented with wireless techniques (e.g., microwave, infrared or other transmission techniques). The series of computer instructions embodies all or part of the functionality previously described herein with respect to the system. Those skilled in the art should appreciate that such computer instructions can be written in a number of programming languages for use with many computer architectures or operating systems. Furthermore, such instructions may be stored in any memory device, such as semiconductor, magnetic, optical or other memory devices, and may be transmitted using any communications technology, such as optical, infrared, microwave, or other transmission technologies. It is expected that such a computer program product may be distributed as a removable medium with accompanying printed or electronic documentation (e.g., shrink wrapped software), preloaded with a computer system (e.g., on system ROM or fixed disk), or distributed from a server or electronic bulletin board over the network (e.g., the Internet or World Wide Web). Of course, some embodiments of the invention may be implemented as a combination of both software (e.g., a computer program product) and hardware. Still other embodiments of the invention are implemented as entirely hardware, or entirely software (e.g., a computer program product).

Although various exemplary embodiments of the invention have been disclosed, it should be apparent to those skilled in the art that various changes and modifications can be made which will achieve some of the advantages of the invention without departing from the true scope of the invention.

What is claimed is:

1. A signal processing system for signal processing comprising a bilateral hearing implant system having left side and right side hearing implants with electrode contacts, the signal processing system further comprising:

at least one sensing microphone for each of the left side and right side hearing implants configured for sensing a sound environment for that hearing implant to develop a corresponding microphone signal output;

a filter bank for each of the left side and right side hearing implants configured for processing the microphone signal to generate a plurality of band pass signals for that hearing implant, wherein each band pass signal represents an associated band of audio frequencies;

an interaural coherence analysis module configured to receive input signals from each of the left side and right side hearing implants including the microphone signals and the band pass signals and configured to analyze the input signals to produce an interaural coherence signal output characterizing reverberation-related similarity of the input signals;

a pulse timing and coding module for each of the left side and right side hearing implants configured for processing the band pass signals to develop stimulation timing signals, wherein the processing includes selecting from the band pass signals a subset of one or more selected band pass signals, and wherein for the one or more selected band pass signals, wherein the processing includes using an envelope gating function developed from the interaural coherence signal; and a pulse generation module for each of the left side and right side hearing implants configured for processing the stimulation timing signals to develop electrode stimulation signals to electrode contacts of the left side and right side hearing implants implanted in a patient cochlea for perception as sound.

2. The signal processing system according to claim 1, wherein the envelope gating function is configured to modify band pass envelope components of the band pass signals to produce gated envelopes that are applied to the stimulation timing signals.

3. The signal processing system according to claim 2, wherein the gating function uses a gating threshold value such that:
   when a band pass envelope is greater than or equal to the gating threshold value, the gated envelope equals the band pass envelope, and
   when a band pass envelope is less than the gating threshold value, the gated envelope is zero.

4. The signal processing system according to claim 2, wherein the gating function is configured to produce variable amplitude gated envelopes that increase in amplitude as the gating function increases in amplitude.

5. The signal processing system according to claim 1, wherein the pulse timing and coding module is configured to use Continuous Interleaved Sampling (CIS) to develop the electrode stimulation signals.

6. The signal processing system according to claim 1, wherein the pulse timing and coding module is configured to use Channel Specific Sampling Sequences (CSSS) to develop the electrode stimulation signals.

7. The signal processing system according to claim 1, wherein the interaural coherence module is configured to select one or more of the input signals to analyze using a switching arrangement controlled as a function of Auditory Scene Analysis (ASA).

8. The signal processing system according to claim 1, wherein the interaural coherence module is configured to select one or more of the input signals to analyze based on a configurable input switch set during a user fitting process.

9. A computer based method implemented using at least one hardware implemented processor for signal processing comprising a bilateral hearing implant system having left side and right side hearing implants with electrode contacts, the method comprising:
   for each of the left side and right side hearing implants, using the at least one hardware implemented processor to process an input sound signal with a filter bank to generate a plurality of band pass signals, wherein each band pass signal represents an associated range of audio frequencies, and wherein each band pass signal has characteristic temporal fine structure features and a characteristic band pass envelope reflecting time varying amplitude of the band pass signal;
   using the at least one hardware implemented processor to analyze input signals from each of the left side and right side hearing implants including the input sound signals and the band pass signals to produce an interaural coherence signal output characterizing reverberation-related similarity of the input signals;
   for each of the left side and right side hearing implants, selecting from the band pass signals a subset of one or more selected band pass signals, and for the one or more selected band pass signals, using the at least one hardware implemented processor to processing the band pass signals in a time sequence of stimulation frames to develop stimulation timing signals, wherein for each stimulation frame the processing includes using an envelope gating function developed from the interaural coherence signal; and
   for each hearing implant using the at least one hardware implemented processor to process the stimulation timing signals to develop electrode stimulation signals to electrode contacts of the left side and right side hearing implants implanted in a patient cochlea for perception as sound.

10. The method according to claim 9, wherein the envelope gating function is configured to modify band pass envelope components of the band pass signals to produce gated envelopes that are applied to the stimulation timing signals.

11. The method according to claim 10, wherein the gating function uses a gating threshold value such that:
   when a band pass envelope is greater than or equal to the gating threshold value, the gated envelope equals the band pass envelope, and
   when a band pass envelope is less than the gating threshold value, the gated envelope is zero.

12. The method according to claim 10, wherein the gating function is configured to produce variable amplitude gated envelopes that increase in amplitude as the gating function increases in amplitude.

13. The method according to claim 9, wherein the stimulation timing signals are developed using Continuous Interleaved Sampling (CIS).

14. The method according to claim 9, wherein the stimulation timing signals are developed using Channel Specific Sampling Sequences (CSSS).

15. The method according to claim 9, wherein one or more of the input signals is selected for analyzing using a switching arrangement controlled as a function of Auditory Scene Analysis (ASA).

16. The method according to claim 9, wherein one or more of the input signals is selected for analyzing based on a configurable input switch set during a user fitting process.

* * * * *